United States Patent
Burgo

(10) Patent No.: US 7,317,068 B2
(45) Date of Patent: Jan. 8, 2008

(54) COMPLEX POLYOL POLYESTER POLYMER COMPOSITIONS FOR USE IN PERSONAL CARE PRODUCTS AND RELATED METHODS

(75) Inventor: Rocco Burgo, Mullica Hill, NJ (US)

(73) Assignee: Inolex Investment Corporation, Wilmington, DE (US)

( * ) Notice: Subject to any disclaimer, the term of this patent is extended or adjusted under 35 U.S.C. 154(b) by 0 days.

(21) Appl. No.: 11/169,997

(22) Filed: Jun. 28, 2005

(65) Prior Publication Data

US 2005/0288478 A1 Dec. 29, 2005

Related U.S. Application Data

(60) Provisional application No. 60/583,487, filed on Jun. 28, 2004.

(51) Int. Cl.
*C08G 63/02* (2006.01)

(52) U.S. Cl. .................. 528/272; 424/70.11; 424/401; 424/402; 424/403; 424/404; 510/130; 510/131; 528/271

(58) Field of Classification Search ............. 424/70.11, 424/401, 402, 403, 404; 510/130, 131; 528/271, 528/272

See application file for complete search history.

(56) References Cited

U.S. PATENT DOCUMENTS 5,391,664 A * 2/1995 Takei et al. ................. 526/210

OTHER PUBLICATIONS

Product Information for Schercemol™ DISM Ester from Noveon, Inc. (Jun. 2005 Edition) (1 page).
Product Information for Ultracas® G-20 Guerbet Ester from Noveon, Inc. (Sep. 17, 2002 Edition) (2 pages).
Product Information for Cosmol 42 from Ikeda Corporation (website printed Oct. 18, 2005) (2 pages).
Product Information for Cosmol 43 from Ikeda Corporation (website printed Oct. 18, 2005) (2 pages).
Product Information for Cosmol 222 from Ikeda Corporation (website printed Oct. 18, 2005) (2 pages).
CRODA Product Catalog: 2003 Year in Review, Cromollient DP3A (9 pages) (see p. 5).

* cited by examiner

*Primary Examiner*—Terressa Boykin
(74) *Attorney, Agent, or Firm*—Flaster/Greenberg P.C.

(57) ABSTRACT

Polyol polyester polymers are provided which are useful for personal care formulations and products containing such formulations. The polyol polyester polymers include a reaction product of at least one polyfunctional alcohol, at least one polyfunctional carboxylic acid and at least one monofunctional carboxylic acid, wherein the polyfunctional alcohol includes about two to about ten carbon atoms, the polyfunctional carboxylic acid includes one to about thirty-six carbon atoms and the monofunctional carboxylic acid includes about four to about twenty-four carbon atoms. Such polyol polyester polymers can have a dynamic viscosity at 25° C. of about 200 to about 5000 centipoise and a hydroxyl value of about 40 to about 300 KOH/g.

21 Claims, No Drawings

COMPLEX POLYOL POLYESTER POLYMER COMPOSITIONS FOR USE IN PERSONAL CARE PRODUCTS AND RELATED METHODS

CROSS-REFERENCE TO RELATED APPLICATIONS

This application claims the benefit of priority under 35 U.S.C. § 119(e) based upon U.S. Provisional Patent Application No. 60/583,487, filed Jun. 28, 2004, the entire disclosure of which is incorporated herein by reference.

BACKGROUND OF THE INVENTION

This invention relates to high viscosity polar oils useful for use in cosmetics and toiletries comprising complex polyol polyester polymers and blends thereof, their method of production, and their use.

Both natural and synthetic ester oils are used extensively in cosmetic and toiletry applications. In contrast to mineral oils, ester oils contain the polar ester linkage that provides substantivity to the skin and to the hair by electrostatic attraction. The ester oils provide a variety of benefits such as skin lubrication, moisturization, conditioning, and modification of the initial feel and after-feel of cosmetic formulations. Furthermore, they provide conditioning and shine enhancement to the hair. Many ester oils are available to the industry, each providing benefits that can be predicted through examination of basic physical properties such as viscosity, viscosity temperature behavior, melting point, density, hydrophilic/lipophilic balance and/or solubility parameter, refractive index, and others. Due to the fundamental structure of non-polymeric ester oils and the limitation of commercially available carboxylic acids and alcohols available for their production, the viscosity range for these oils is limited.

In certain instances, a higher viscosity which is not obtainable through simple ester chemistry is a desirable benefit. *Ricinus communis* seed oil (castor oil) is unique among the natural triglyceride oils because its high viscosity (approximately 6 to 8 poises at 25° C.) facilitates a delay in the settling of pigments in color cosmetic product, and acts to delay the tendency of the formulated cosmetic product to smear or run off of the skin. Castor oil primarily consists of glyceryl triesters of ricinoleic acid (an unsaturated fatty acid). It is therefore a molecule that contains three hydroxyl groups, making it significantly more polar than most triglyceride oils. This higher polarity increases its "solvent power" (the ability of a solvent to dissolve many polar formulation ingredients, particularly organic staining dyes that are used extensively in color cosmetics). Castor oil is currently used extensively in personal care products for topical application to the skin such as lipsticks, lip glosses, eyebrow pencils, eyeliners, eye shadows, mascaras, face powders, moisturizing creams, lotions, gels, and suntan/sunscreen products. It is also used in a variety of hair care applications such as conditioning shampoos, conditioners, hair waxes, hair dyes and colors, hair bleaches, hair tonics and grooming products, and hair sprays. It is also used in bath and body care formulations such as bath oils, shaving preparation products, and bath soaps and detergents.

Castor oil has disadvantages in that it tends to have a disagreeable odor and distinctive unpleasant taste, described by some as "bitter" or "sickly." Castor oil is also poorly resistant to autoxidation due to unsaturation in the fatty alkyl portions of the molecule, and thus will tend to quickly develop further intensified odor and taste when heated, which is necessary such as in the production of many personal care products, particularly lipsticks. For example, if significant oxidation occurs during lipstick processing, the molten lipstick can tend to increase and/or change in color, to increase viscosity, and to form insoluble precipitates and films. At room temperature, degradation still occurs but at a slower rate; however, the rate can be quite variable depending upon the thermal and oxidative history of the oil prior to use. This can lead to major variation in the batch to batch stability and therefore the shelf life of the article produced.

To improve its resistance to autoxidation, castor oil can be hydrogenated to reduce its unsaturation; however, to achieve acceptable oxidation resistance, the required level of reduction in unsaturation by hydrogenation is such that its melting point increases resulting in a product that is solid at room temperature, which is not useful for many applications. In color cosmetic products, castor oil can retard the penetration of oils into lumps of dry pigment during the mixing operation, and can cause a feeling of friction or drag when the cosmetic product is applied.

Additionally, the United States is totally dependent upon imports to meet industry demands for castor oil, as the castor bean is only cultivated significantly in India, and South America.

Despite these serious technical and economic disadvantages, castor oil continues to be used extensively because of the absence of a suitable replacement in terms of performance and/or cost. Therefore, there is a need in the cosmetic industry for a product that has a similar viscosity and polarity to castor oil, has good solvent power for staining dyes, has an equivalent or higher viscosity index than castor oil, exhibits reduced drag, has less odor and color, has greater resistance to autoxidation, can be sourced dependably, while remaining cost effective.

As of yet, this need is unfulfilled. Research has been conducted into the development of alternative seed crops that can deliver a natural oil that has similar characteristics to castor oil. Increased cultivation of castor beans in the United States is infeasible since the seed, leaves, and stem of the castor plant are poisonous to humans and livestock; the ingestion of even one seed can be fatal to humans. Seeds of the castor plant contain ricin, a powerful toxin that can induce hepatic lipid peroxidation, glutathione depletion, and severe liver necrosis and is considered by the U.S. government to be an agent of biological warfare. Thus, those seeking to cultivate castor beans in the U.S. may be subject to various regulations and restrictions.

Currently, a program is in place to develop the cultivation of *Lesquerella fendleri* (bladder pod), since its seeds contain fatty acids that are similar to those present in castor oil. However, progress has been slow in the development of this alternative, and field and greenhouse experiments have shown that *Lesquerella* production under the conditions prevailing in the United States may not be feasible.

Higher viscosity synthetic esters have been developed, such as pentaerythritol tetraisostearate (CROMAMOL® PTIS, Croda Corporation, Parsippany, N.J., United States of America), PURESYN® ME100, PURESYN® ME450 (ExxonMobil Corporation, Edison, N.J., United States of America), and LEXFEEL® 350 (Inolex Chemical Company, Philadelphia, Pa., United States of America), which provide the viscosity needed for effective pigment dispersion; however, they are too low in polarity as they do not contain the hydroxyl functionality that is required to be a suitable replacement for castor oil.

BRIEF SUMMARY OF THE INVENTION

The present invention includes a polyol polyester polymer comprising a reaction product of at least one polyfunctional alcohol, at least one polyfunctional carboxylic acid, and at least one monofunctional carboxylic acid; wherein the polyfunctional alcohol comprises about two to about ten carbon atoms; the polyfunctional carboxylic acid comprises one to about thirty-six carbon atoms; the monofunctional carboxylic acid comprises about four to about twenty-four carbon atoms; and the polyol polyester polymer has a dynamic viscosity at 25° C. of about 200 to about 5000 centipoise and a hydroxyl value of about 40 to about 300 mg KOH/g.

The present invention also includes a method of preparing a personal care product, comprising incorporating a polyol polyester polymer into a personal care formulation, wherein the polyol polyester polymer is a reaction product of at least one polyfunctional alcohol, at least one polyfunctional carboxylic acid, and at least one monofunctional carboxylic acid, and wherein the polyfunctional alcohol comprises about two to about ten carbon atoms, the polyfunctional carboxylic acid comprises one to about thirty-six carbon atoms, and the monofunctional carboxylic acid comprises about four to about twenty-four carbon atoms.

Also included within the invention is a personal care product which comprises (a) a polyol polyester polymer comprising the product of esterification of at least one polyfunctional alcohol, at least one polyfunctional carboxylic acid, and at least one monofunctional carboxylic acid wherein: (i) the polyfunctional alcohol comprises about two to about ten carbon atoms; (ii) the polyfunctional carboxylic acid comprises one to about thirty-six carbon atoms; (iii) the monofunctional carboxylic acid comprises about four to about twenty-four carbon atoms; (iv) the resulting polyol polyester has a dynamic viscosity at 25° C. of about 200 to about 5000 centipoise; (v) the resulting polyol polyester polymer has a hydroxyl value of about 40 to about 300 mg KOH/g; and (b) a personal care formulation, wherein the product is substantially free of castor oil.

DETAILED DESCRIPTION OF THE INVENTION

The present invention provides a family of polyols and carboxylic acids that exhibit the desirable viscosity, viscosity temperature behavior, solvent power, oxidation resistance, odor, and color as compared to castor oil when the polyols and carboxylic acids are esterified.

Accordingly, one embodiment of the present invention is a component and/or components of a formulation for use in personal care products comprising polyol polyester polymers, preferably liquid complex polyol polyester polymers of (a) at least one polyol, (b) at least one polyfunctional carboxylic acid, and (c) at least one monofunctional carboxylic acid. The polyol polyester polymers and/or blends thereof of the invention have similar viscosity and solvent power of castor oil, and superior odor, color, taste, and oxidation resistance, resulting in products that can be used in personal care compositions.

As used herein, "polyol" is a polyfunctional alcohol preferably including about two to about ten carbon atoms, having two or more OH groups and including optionally one or more additional functional groups and which may be, for example, aliphatic, saturated, linear and/or branched. Typical polyols include, but are not limited to diols, triols, tetraols, pentaols, hexaols that may be linear and/or branched, aliphatic and/or aromatic. Preferred polyols include glycerol, pentaerythritol, dipentaerythrityl, tripentaerythritol, trimethylolpropane, neopentyl glycol, propylene glycol, 1,3-butylene glycol, 2-methyl-1,3-propanediol, dipropylene glycol, ethylene glycol, cyclohexanedimethanol, butyl ethyl propanediol, and derivatives and combinations thereof.

As used herein, "polyfunctional carboxylic acid" is a carboxylic acid with at least two carboxylic acid groups and optionally one or more additional functional groups, including functionalized and non-functionalized dicarboxylic acids. Polyfunctional carboxylic acids can be aliphatic, aromatic, saturated, linear and/or branched. Preferably, the polyfunctional carboxylic acids used herein have one to about thirty six carbon atoms. Dicarboxylic acids are most preferred. Non-limiting examples of polyfunctional carboxylic acids which may be used in the polymers formed herein include carbonic acid, hexanedioic acid, dimer acid, azelaic acid, sebacic acid, dodecanedioic acid, glutaric acid, succinic acid, phthalic acid, isophthalic acid, terephthalic acid, 2,6-naphthalene dicarboxylic acid, and derivatives and combinations thereof.

"Monofunctional carboxylic acids" as used herein are organic acids comprising a carboxylic acid group. Monofunctional carboxylic acids useful herein, can be aliphatic, aromatic, saturated, linear and/or branched. The preferred monofunctional carboxylic acids have from about four to about twenty-four carbon atoms. Non-limiting examples of suitable monofunctional carboxylic acids for use in the polymers herein include isobutyric acid, benzoic acid, 2-ethyl butyric acid, hexanoic acid, heptanoic acid, 2-ethylhexanoic acid, octanoic acid, nonanoic acid, 3,5,5-trimethylhexanoic acid, isononanoic acid, decanoic acid, isooctadecanoic acid, dodecanoic acid, 2-methyl butyric acid, isopentanoic acid, pentanoic acid, 2-methyl pentanoic acid, 2-methyl hexanoic acid, isooctanoic acid, undecylinic acid, isolauric acid, isopalmitic acid, isostearic acid, behenic acid, and derivatives and combinations thereof.

In one embodiment the polyol polyesters polymers include controlled polarity, complex polyol polyester polymers for use in cosmetics and toiletries. In particular, it is preferred that such polyol polyester polymers are complex polyol polyester polymers that compare favorably to castor oil in similar applications in at least one or more of the following performance properties: viscosity, viscosity/temperature behavior, solvent power, odor, color, taste, and oxidation resistance.

More particularly, such polymers include complex polyol polyester polymers derived from the esterification of at least one $C_2$ to $C_{10}$ polyol with at least one $C_1$ to $C_{36}$ dicarboxylic acid, and at least one $C_4$ to $C_{24}$ carboxylic acid. Such polymers preferably have a hydroxyl value which is controlled to be about 40 to about 300 mg KOH/g, and more preferably about 60 to about 150 mg KOH/g. Such preferred polyol polyester polymers also preferably have a dynamic viscosity at 25° C. of about 200 to about 5000 centipoise, preferably about 400 to about 2000 centipoise.

Personal care products as used herein include any product, whether known in the art or to be developed, that includes a composition that is used or marketed as a material to be applied to the skin, hair, nails and/or the stratum corneum of human or animal subjects for cosmetic, aesthetic, and/or therapeutic effects, regardless of the delivery form of the product and/or related composition, and may include phases or intermediate preparations ultimately formulated into personal care products. Such products include grooming and personal care products, such as soaps, cleansers, shampoos, skin or hair conditioners, shaving creams, lotions, gels, hair sprays, tonics, mousses, pomades, lacquers, antiperspirants, deodorants, skin lotions, sunscreens, creams, ointments, and nail and cuticle care products, such as polishes and creams. Also included are color and/or reflectivity imparting cosmetics (decorative cosmetics), such as lipsticks, lip glosses, mascaras, cream blushes, foundations, eye shadows, and other decorative cosmetics.

Personal care formulations include any formulations, known or to be developed in the art, for use in personal care products. Such formulations include components that will be combined with, included with and/or incorporate within them at least one of the polyol polyester polymers described herein. Exemplary formulations include those useful for forming soap (liquid, solid, foam, gel or mousse), cleansers, creams, lotions, ointments, suspensions, shampoos, deodorants, antiperspirants, conditioning products for the hair, skin, and nails, and decorative cosmetics (i.e., those that impart color or reflectivity to the hair, skin or nails upon application). The personal care formulations used in the invention may include organic components, inorganic components, color active ingredients (e.g., pigments and dyes), at least one therapeutic active ingredient (e.g., vitamins, alpha hydroxy acids, corticosteroids, amino acids, collagen, retinoids, antimicrobial compounds, pain relievers, antihistamines, antifungals and the like), sunscreens and/or UV absorbing or blocking compounds, reflective compounds, oils such as vegetable or mineral oils, film formers, high viscosity oils, thixotropic agents, high molecular weight esters, antiperspirant active ingredients, glycol solutions, water, alcohol, emulsifiers, gelans, emollients, water, polymers, hydrocarbons, conditioning agents, preservatives and/or aliphatic esters. Personal care products and formulations may be prepared using any suitable amounts and ratios of components as commonly known and used and/or to be developed in the personal care arts.

The complex polyol polyester polymers described herein are derived as reaction products from the reaction of polyols, polyfunctional carboxylic acids and monofunctional carboxylic acids. Properties of these polyol polyester polymers such as viscosity, viscosity temperature behavior, solvent power, odor, color, taste, and oxidation resistance can be modified by careful selection of the polyol, polyfunctional carboxylic acid, and monofunctional carboxylic acid used to prepare the polyol polyester polymer, by control of the hydroxyl functionality, and by the manufacturing process employed.

One preferred, non-limiting example polymer according to this disclosure is controlled polarity complex polyol polyester polymer A (CPCPPPA), which is derived by the esterification of pentaerythritol, hexanedioic acid, heptanoic acid, octanoic acid, and decanoic acid, utilizing a ratio of reactants such that the product has a viscosity similar to that of castor oil. The viscosity can be adjusted by adjusting the molecular weight of the polymer, with higher molecular weights giving higher viscosities. The molecular weight and hydroxyl number can be calculated in a manner known in the polymeric arts based on the amount of initial reactants. CPCPPPA is a water white, odorless, tasteless liquid with a viscosity of 500 centipoises at 25° C. CPCPPPA can be used as a direct replacement for castor oil in a formulation for color cosmetics. CPCPPPA provides excellent reduction in the settling rate of pigments, high solvent power for bromo acid, and superior viscosity index, color, odor, taste, and oxidation resistance when compared to castor oil. It is preferred herein that personal care formulations and products are substantially free of castor oil (i.e., that to the extent castor oil is present, it is present in only minor amounts and in a ratio of at least 75:25 polyol polyester polymer to castor oil), and more preferably that such formulations and products are fully free of castor oil (i.e., it is a direct replacement). However, it should be understood that, while not preferred, such polyol polyester polymers can be used in formulations in which castor oil is present within the scope of the invention.

Another non-limiting example of the polymers described herein is controlled polarity complex polyol polyester polymer B (CPCPPPB) which is derived by the esterification of pentaerythritol, hexanedioic acid, heptanoic acid, octanoic acid, and decanoic acid, utilizing a slightly different ratio of reactants than CPCPPPA such that the product has a viscosity similar to that of castor oil. CPCPPPB is also a water white, odorless, tasteless liquid, however the viscosity is about 700 centipoises at 25° C.

The invention will now be further described in conjunction with the following non-limiting examples:

EXAMPLE 1

A Replacement Composition that can be Used to Replace Castor Oil in a Personal Care Product:

Pentaerythritol, hexanedioic acid, heptanoic acid, octanoic acid, and decanoic acid were charged to a stirred batch reactor in a molar ratio of 2.1:1.0:4.8:0.05:0.05 and heated with inert gas sparging to about 180° C.-230° C. in the presence of a small quantity of catalyst and activated charcoal. The acid value was monitored, and the reaction was stopped before the acid value reached 1 mg KOH/g. The resulting controlled polarity complex polyol polyester polymer A (CPCPPPA) was then heated to about 160° C. and steam stripped under a vacuum of at least about 740 mm Hg. The purified CPCPPPA was then filtered. Table 1 shows the properties obtained.

TABLE 1

| Property | Value |
|---|---|
| Appearance | Clear, White Viscous Liquid |
| Color, APHA | 29 |
| Total Acid Number, mg KOH/g | 0.13 |
| Hydroxyl Number, mg KOH/g | 87.7 |
| Odor | Odorless |
| Taste | Tasteless |
| Viscosity@25° C., cps | 505 |
| Viscosity Index | 141 |
| Molecular Weight, Daltons | 858 |

In this and the subsequent examples herein, certain properties were tested using standard test methods of the American Society of Testing and Materials (ASTM), West Conshohocken, Pa., United States. Kinematic viscosity was tested according to ASTM D-445-97 (1997); Color was measured using ASTM D-1209; Total Acid Number (Acid Value) was determined using ASTM D-974-95 (1995); and Viscosity Index (VI) was determined using ASTM D-2270. Hydroxyl number was determined using a modified version of AOCS (American Oil Chemists Society, Champaign, Ill., United States of America) official method number Cd-13-60, the content of each such standard are incorporated herein in relevant part by reference. Odor absence was determined by subjective olfactory evaluation, and taste was determined by subjective organoleptic evaluation. Molecular weight was calculated based upon the ratio of reactants employed.

EXAMPLE 2

A Replacement Composition that can be Used to Replace Castor Oil in a Personal Care Product:

Pentaerythritol, hexanedioic acid, heptanoic acid, octanoic acid, decanoic acid were charged to a stirred batch reactor in a molar ratio of 1.8:1.0:4.0:0.01:0.01 and heated with inert gas sparging to about 160° C.-225° C. in the presence of a small quantity of catalyst and antioxidant. The acid value was monitored, and the reaction was stopped when the acid value reached 1 mg KOH/g or lower. The resulting controlled polarity complex polyol polyester polymer B (CPCPPPB) was heated to about 160° C. and steam stripped under a vacuum of 740 mmHg or higher. The purified CPCPPPB was then filtered. Table 2 shows the properties obtained.

TABLE 2

| Property | Value |
| --- | --- |
| Appearance | Clear, White Viscous Liquid |
| Color, APHA | 62 |
| Total Acid Number, mg KOH/g | 0.36 |
| Hydroxyl Number, mg KOH/g | 88.1 |
| Odor | Odorless |
| Taste | Tasteless |
| Viscosity@25° C., cps | 700 |
| Viscosity Index | 146 |

EXAMPLE 3

A Replacement Composition that can be Used to Replace Castor Oil in a Personal Care Product.

Table 3 lists the properties of CPCPPPA and CPCPPPB as compared to castor oil.

TABLE 3

| Property | CPCPPPA | CPCPPPB | Castor Oil |
| --- | --- | --- | --- |
| Appearance | Colorless | Colorless | Yellow |
| Odor | Odorless | Odorless | Waxy, rancid |
| Taste | Tasteless | Tasteless | Sickly |
| Viscosity@25° C., cps | 500 | 700 | 760 |
| Viscosity Index | 141 | 146 | 77 |

The following formulations show the use of the ester of this invention in exemplary toiletry and cosmetic applications. In the following examples, the names for each ingredient other than the blend of the invention are the CTFA (Cosmetics, Toiletry and Fragrance Association, Inc.) names.

EXAMPLE 4

Preparation of Personal Care Products that are Lipsticks

The following compositions illustrate the preparation of two lipsticks, Formulas X and Y, illustrating how castor oil can be replaced by CPCPPPA resulting in a lipstick with significantly improved odor and taste, and none of the other technical or economic disadvantages associated with castor oil. Table 4 shows a comparison of Formula X (including CPCPPPA) and Formula Y (including castor oil).

TABLE 4

| Ingredients | Formula X Parts by weight | Formula Y Parts by Weight |
| --- | --- | --- |
| CPCPPPA | 54.50 | — |
| Castor Oil | — | 54.50 |
| Red # 7 Calcium Lake (and) Dipentaerythrityl Hexa C5-9 Acid Esters | 12.00 | 12.00 |
| Dipentaerythrityl Hexa C5-9 Acid Esters | 4.00 | 4.00 |
| Neopentyl Glycol Diheptanoate | 7.00 | 7.00 |
| Ozokerite Wax | 3.00 | 3.00 |
| Microcrystalline Wax | 3.00 | 3.00 |
| Candelilla Wax | 9.00 | 9.00 |
| Iron oxides (and) Mica (Colorona Bordeaux) | 7.00 | 7.00 |
| Vitamin E Acetate | 0.50 | 0.50 |

In Formula X, the above listed components were formed into the composition by the following procedure. Candelilla wax, ozokerite wax, microcrystalline wax, dipentaerythrityl hexa C5-9 acid esters, dipentaerythrityl hexa C5-9 acid esters (and) Red #7 calcium lake, and CPCPPPA, were combined in a vessel and warmed to about 80° C. to about 85° C. with gentle agitation until a uniform solution is obtained. Iron oxides (and) mica (colorona bordeaux) and tocopheryl acetate were individually added to the mixture with moderate agitation until a uniform solution was obtained. The heating was stopped and the solution was allowed to cool to about 70° C. to about 75° C. with gentle agitation. The resulting mixture was poured into an about 40° C. to about 45° C. lipstick mold and allowed to cool to room temperature. Formula Y was prepared in accordance with the same procedure as used in Formula X, however castor oil was substituted for CPCPPPA. Formula X was then compared to Formula Y regarding essential properties for lipsticks. In the comparison, a numerical scale was developed relating to the degree of each of the properties. The scale is defined as 1="none", 2="slight", 3="average", 4="moderate", and 5="high." Table 5 shows a comparison of the properties of Formula X lipstick to the Formula Y lipstick:

TABLE 5

| Property | Formula X | Formula Y |
| --- | --- | --- |
| Degree of Slip | 4 | 3 |
| Degree of Gloss | 2 | 2 |
| Degree of Tackiness | 3 | 3 |
| Deposition of Color | 5 | 4 |
| Evenness of Color | 4 | 3 |
| Degree of Odor | 2 | 4 |
| Degree of Taste | 2 | 4 |

As can be seen in the data provided in Table 5, Formula X in which castor oil was replaced by CPCPPPA provided better slip, deposition of color, and evenness of color. More importantly, Formula X was significantly lower in both odor and taste when compared to Formula Y, the castor oil containing formula.

EXAMPLE 5

Preparation of a Personal Care Product that is a Lipstick

The following composition illustrates the preparation of an improved lipstick that is odorless and tasteless utilizing CPCPPPA. The composition is shown below in Table 6.

TABLE 6

| | Parts By Weight |
|---|---|
| Part A | |
| Euphorbia Cerifera (Candelilla) Wax | 11.00 |
| Ozokerite | 3.00 |
| Microcrystalline Wax | 3.00 |
| Dipentaerythrityl Hexa C5-9 Acid esters | 6.00 |
| Dipentaerythrityl Hexa C5-9 Acid esters (and) Red #7 Calcium Lake 40% | 12.00 |
| CPCPPPA | 57.50 |
| Part B | |
| Tocopheryl Acetate | 0.50 |
| Mica (and) Titanium Dioxide | 4.00 |
| Mica (and) Iron Oxides | 3.00 |

The above listed components in Table 6 were formed into the composition by the following procedure. Part A, *euphorbia cerifera* (candelilla) wax, ozokerite, microcrystalline wax, dipentaerythrityl hexa C5-9 acid esters, dipentaerythrityl hexa C5-9 acid esters (and) Red #7 calcium lake, and CPCPPPPA, were combined in a vessel and warmed to about 80° C. to about 85° C. with gentle agitation until a uniform solution is obtained. Part B, mica (and) titanium dioxide, mica (and) iron oxides, and tocopheryl acetate were individually added to Part A with moderate agitation until a uniform solution is obtained. The heating was stopped and the solution of Part A and Part B was allowed to cool to about 70° C. to about 75° C. with gentle agitation. The resulting mixture was poured into about 40° C. to about 45° C. lipstick mold and allowed to cool to room temperature.

EXAMPLE 6

Preparation of a Personal Care Product that is a Moisturizing Cream

The following example illustrates the preparation of a personal care composition of the invention that is a moisturizing cream for the skin. The formulation preparation information is shown below in Table 7.

TABLE 7

| Ingredients | Parts by weight |
|---|---|
| Part A | |
| Deionized water | 77.60 |
| Propylene glycol | 4.00 |
| Methylparaben | 0.25 |
| Propylparaben | 0.05 |
| Part B | |
| Cetearyl Alcohol (and) ceteareth-20 | 3.00 |
| Glyceryl stearate | 1.50 |
| Glyceryl stearate (and) PEG-100 stearate | 2.00 |
| Neopentyl glycol diheptanoate | 6.00 |
| CPCPPPB | 4.00 |
| Part C | |
| Tocopheryl acetate | 0.30 |
| Retinyl palmitate | 0.30 |
| DL-panthenol (and) propylene glycol | 1.00 |

The above listed components in Table 7 were formed into the composition by the following procedure. The components from Part A, i.e., deionized water, propylene glycol, methylparaben and propylparaben, were combined in a vessel and warmed to about 70° C. to about 75° C. with vigorous agitation until a clear, uniform solution was obtained. The components in Part B, i.e., cetearyl alcohol (and) ceteareth-20, glyceryl stearate, glyceryl stearate (and) PEG-100 stearate, neopentyl glycol diheptanoate and CPCP-PPB, were combined in a separate vessel with gentle agitation and warmed to about 70° C. to about 75° C. until a clear solution was obtained. The solution of Part B was added to Part A with high shear mixing. The high shear mixing and heating were stopped and the solution was allowed to cool to about 40° C. to about 45° C. The components of Part C, i.e., tocopheryl acetate, retinyl palmitate, DL-panthenol (and) propylene glycol were individually added to combined Parts A and B with gentle agitation. The solution was allowed to cool to room temperature with gentle agitation. The resulting emulsion was poured into canisters.

EXAMPLE 7

Preparation of a Personal Care Product that is a Hair Styling Wax

The following composition illustrates the preparation of a personal care composition of the invention that is a hair styling wax with the components for preparation listed in Table 8 below.

TABLE 8

| Ingredients | Parts by weight |
|---|---|
| CPCPPPA | 5.00 |
| Adipic acid/diethylene glycol/glycerin crosspolymer | 1.00 |
| Neopentyl glycol diheptanoate (and) isododecane | 76.90 |
| Propylparaban | 0.10 |
| Ozokerite wax | 12.00 |
| Laureth-7 | 5.00 |

The above listed components in Table 8 are formed into the composition by the following procedure. CPCPPPA, adipic acid/diethylene glycol/glycerin crosspolymer, neopentyl glycol diheptanoate (and) isododecane, propylparaben, ozokerite wax, and laureth-7 are combined in a vessel and warmed to about 80° C. to about 85° C. with gentle agitation until a clear, uniform solution is obtained. The heating is stopped and the solution is allowed to cool to about 60° C. to about 65° C. with gentle agitation. The mixture is then poured into a suitable container and allowed to cool to room temperature.

EXAMPLE 8

Preparation of an Eye Shadow Personal Care Product

The following composition shown below in Table 9 illustrates the preparation of a personal care composition of the invention that is an eye shadow.

TABLE 9

| Ingredients | Parts by weight |
|---|---|
| Talc | 40.90 |
| Silica | 10.00 |
| Mica (and) Titanium Dioxide | 37.00 |
| (and) Iron Oxide (and) Silica | |
| Propylparaben | 0.10 |
| CPCPPPA | 12.00 |

The above listed components in Table 9 were formed into the composition by the following procedure. In an appropriate mixing vessel, talc, silica mica (and) titanium dioxide (and) iron oxide (and) silica, and propylparaben were combined. They were mixed until uniform. Once uniform, CPCPPPA was added drop-wise until a uniform powder was achieved. The resulting mixture was placed into suitable containers.

EXAMPLE 9

Preparation of a Hair Care Conditioner Formulation

The following composition shown below in Table 10 illustrates the preparation of a personal care composition according to the invention that is hair care conditioning formulation.

| Ingredients | Parts By Weight |
|---|---|
| Part A | |
| Water | 86.14 |
| Methylparaben | 0.25 |
| Propylparaben | 0.10 |
| Tetrasodium EDTA | 0.15 |
| Cocamidopropyl PG-Dimonium Chloride | 2.36 |
| Part B | |
| Cetyl Alcohol | 3.00 |
| CPCPPPA | 4.00 |
| Glyceryl Stearate (and) PEG-100 Stearate | 4.00 |

The above listed components were formed into the composition by the following procedure. The componetns of Part A, i.e., the deionized water, methylparaben, propylparaben, tetrasodium EDTA, and cocamidopropyl PG-dimonium chloride (and) water were combined in a vessel and warmed to 70° C. to 75° C. with vigorous agitation until a clear, uniform solution was obtained. The Part B components, i.e., the cetyl alcohol, CPCPPPA, and glyceryl stearate (and) PEG-100 stearate were combined in a separate vessel with gentle agitation and warmed to 70° C. to 75° C. until a clear solution was obtained. The solution of Part B was added to Part A with high shear mixing. The high shear mixing was stopped. The heating was stopped, and the solution was allowed to cool to room temperature with gentle agitation. The resulting emulsion was poured into canisters.

While several embodiments have been shown and described in accordance with the invention and use thereof, it is understood that the invention is not limited thereto, but is susceptible to many changes and modifications to one possessing ordinary skill in the art, and therefore the invention is not limited to the details shown and described herein, but covers all such modifications as are encompassed by the scope of the appended claims.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A polyol polyester polymer for use in a personal care product comprising a reaction product of:
at least one polyfunctional alcohol,
at least one polyfunctional carboxylic acid, and
at least one monofunctional carboxylic acid;
wherein the polyol polyester polymer is an esterification reaction product of the at least one polyfunctional alcohol, the at least one polyfunctional carboxylic acid and the at least one monofunctional carboxylic acid and the polyfunctional alcohol comprises about two to about ten carbon atoms; the polyfunctional carboxylic acid comprises one to about thirty-six carbon atoms; the monofunctional carboxylic acid comprises four to about twenty-four carbon atoms; and the polyol polyester polymer has a dynamic viscosity at 25° C. of about 200 to about 5000 centipoise and a hydroxyl value of about 40 to about 300 mg KOH/g.

2. The polyol polyester polymer according to claim 1, wherein the at least one polyfunctional alcohol is selected from the group consisting of aliphatic polyfunctional alcohols, saturated polyfunctional alcohols, branched polyfunctional alcohols, and derivatives and combinations thereof.

3. The polyol polyester polymer according to claim 1, wherein the at least one polyfunctional carboxylic acid is selected from the group consisting of aliphatic polyfunctional carboxylic acids, aromatic polyfunctional carboxylic acids, saturated polyfunctional carboxylic acids, branched polyfunctional carboxylic acids, and derivatives and combinations thereof.

4. The polyol polyester polymer according to claim 1, wherein the at least one monofunctional carboxylic acid is selected from the group consisting of aliphatic monofunctional carboxylic acids, aromatic monofunctional carboxylic acids, saturated monofunctional carboxylic acids, branched monofunctional carboxylic acids, and derivatives and combinations thereof.

5. The polyol polyester polymer according to claim 1, wherein the at least one polyfunctional alcohol is selected from the group consisting of glycerol, pentaerythritol, dipentaerythritol, tripentaerythritol, trimethylolpropane, neopentyl glycol, propylene glycol, 1,3-butylene glycol, 2-methyl-1,3-propanediol, dipropylene glycol, ethylene glycol, cyclohexanedimethanol, butyl ethyl propanediol, and derivatives and combinations thereof.

6. The polyol polyester polymer according to claim 1, wherein the at least one polyfunctional carboxylic acid is selected from the group consisting of carbonic acid, hexanedioic acid, dimer acid, azelaic acid, sebacic acid, dodecanedioic acid, glutaric acid, succinic acid, phthalic acid, isophthalic acid, terephthalic acid, 2,6-naphthalene dicarboxylic acid, and derivatives and combinations thereof.

7. The polyol polyester polymer according to claim 1, wherein the at least one monofunctional carboxylic acid is selected from the group consisting of isobutyric acid, benzoic nonanoic acid, 3,5,5-trimethylhexanoic acid, isononanoic acid, decanoic acid, isooctadecanoic acid, dodecanoic acid, 2-methyl butyric acid, isopentanoic acid, pentanoic acid, 2-methyl pentanoic acid, 2-methyl hexanoic acid, isooctanoic acid, undecylinic acid, isolauric acid, isopalmitic acid, isostearic acid, behenic acid, derivatives and combinations thereof.

8. A method of preparing a personal care product, comprising incorporating a polyol polyester polymer into a personal care formulation, wherein the polyol polyester polymer is an esterification reaction product of at least one polyfunctional alcohol, at least one polyfunctional carboxylic acid, and at least one monofunctional carboxylic acid, and wherein the polyfunctional alcohol comprises two to about ten carbon atoms, the polyfunctional carboxylic acid comprises one to about thirty-six carbon atoms, and the monofunctional carboxylic acid comprises four to about twenty-four carbon atoms.

9. The method according to claim 8, wherein the polyol polyester polymer has a dynamic viscosity at 25° C. of about 200 to about 5000 centipoise and a hydroxyl value of about 40 to about 300 mg KOH/g.

10. The method according to claim 8, wherein the at least one polyfunctional alcohol is selected from the group consisting of aliphatic polyfunctional alcohols, saturated polyfunctional alcohols, branched polyfunctional alcohols, and derivatives and combinations thereof.

11. The method according to claim 8, wherein the at least one polyfunctional carboxylic acid is selected from the group consisting of aliphatic polyfunctional carboxylic acids, aromatic polyfunctional carboxylic acids, saturated polyfunctional carboxylic acids, branched polyfunctional carboxylic acids, and derivatives and combinations thereof.

12. The method according to claim 8, wherein the at least one monofunctional carboxylic acid is selected from the group consisting of aliphatic monofunctional carboxylic acids, aromatic monofunctional carboxylic acids, saturated monofunctional carboxylic acids, branched monofunctional carboxylic acids, and derivatives and combinations thereof.

13. The method according to claim 8, wherein the at least one polyfunctional alcohol is selected from the group consisting of glycerol, pentaerythritol, dipentaerythritol, tripentaerythritol, trimethylolpropane, neopentyl glycol, propylene glycol, 1,3-butylene glycol, 2-methyl-1,3-propanediol, dipropylene glycol, ethylene glycol, cyclohexanedimethanol, butyl ethyl propanediol, and derivatives and combinations thereof.

14. The method according to claim 8, wherein the at least one polyfunctional carboxylic acid is selected from the group consisting of carbonic acid, hexanedioic acid, dimer acid, azelaic acid, sebacic acid, dodecanedioic acid, glutaric acid, succinic acid, phthalic acid, isophthalic acid, terephthalic acid, 2,6-naphthalene dicarboxylic acid, and derivatives and combinations thereof.

15. The method according to claim 8, wherein the at least one monofunctional carboxylic acid is selected from the group consisting of isobutyric acid, benzoic acid, 2-ethyl butyric acid, hexanoic acid, heptanoic acid, 2-ethylhexanoic acid, octanoic acid, nonanoic acid, 3,5,5-trimethylhexanoic acid, isononanoic acid, decanoic acid, isooctadecanoic acid, dodecanoic acid, 2-methyl butyric acid, isopentanoic acid, pentanoic acid, 2-methyl pentanoic acid, 2-methyl hexanoic acid, isooctanoic acid, undecylinic acid, isolauric acid, isopalmitic acid, isostearic acid, behenic acid, derivatives and combinations thereof.

16. The method according to claim 8, wherein the personal care product prepared is substantially free of castor oil.

17. The method according to claim 16, wherein the personal care product prepared is free of castor oil.

18. A personal care product comprising;
a) a polyol polyester polymer comprising a product of esterification of at least one polyfunctional alcohol, at least one polyfunctional carboxylic acid, and at least one monofunctional carboxylic acid, wherein:
  i) the polyfunctional alcohol comprises about two to about ten carbon atoms;
  ii) the polyfunctional carboxylic acid comprises one to about thirty-six carbon atoms;
  iii) the monofunctional carboxylic acid comprises four to about twenty-four carbon atoms;
  iv) the resulting polyol polyester has a dynamic viscosity at 25° C. of about 200 to about 5000 centipoise; and
  v) the resulting polyol polyester polymer has a hydroxyl value of about 40 to about 300 mg KOH/g; and
(b) a personal care formulation, wherein the product is substantially free of castor oil.

19. The personal care product according to claim 18, wherein the product is free of caster oil.

20. The personal care product according to claim 18, wherein the personal care product has a performance characteristic similar to a personal care composition that contains castor oil.

21. The personal care product according to claim 18, wherein the product is selected from the group consisting of soaps, cleansers, shampoos, skin conditioners, hair conditioners, shaving creams, lotions, gels, hair sprays, tonics, mousses, pomades, lacquers, antiperspirants, deodorants, skin lotions, sunscreens, creams, ointments, nail polishes, nail and cuticle creams, lipsticks, lip glosses, mascaras, cream blushes, foundations and eye shadows.

* * * * *